United States Patent
Wang et al.

(10) Patent No.: US 10,233,202 B2
(45) Date of Patent: Mar. 19, 2019

(54) TENOFOVIR MONOBENZYL ESTER PHOSPHAMIDE PRODRUG, PREPARATION METHOD AND USE THEREOF

(71) Applicant: JIANGSU TASLY DIYI PHARMACEUTICAL CO., LTD., Jiangsu (CN)

(72) Inventors: Guocheng Wang, Jiangsu (CN); Huimin Wu, Jiangsu (CN)

(73) Assignee: Jiangsu Tasly Diyi Pharmaceutical Co., LTD., Jiangsu (CN)

( * ) Notice: Subject to any disclaimer, the term of this patent is extended or adjusted under 35 U.S.C. 154(b) by 0 days.

(21) Appl. No.: 15/577,956

(22) PCT Filed: May 26, 2016

(86) PCT No.: PCT/CN2016/083407
§ 371 (c)(1),
(2) Date: Nov. 29, 2017

(87) PCT Pub. No.: WO2016/192560
PCT Pub. Date: Dec. 8, 2016

(65) Prior Publication Data
US 2018/0127445 A1    May 10, 2018

(30) Foreign Application Priority Data
May 29, 2015  (CN) .......................... 2015 1 0290530

(51) Int. Cl.
| | |
|---|---|
| C07F 9/6561 | (2006.01) |
| A61P 31/18 | (2006.01) |
| A61P 31/20 | (2006.01) |
| A61P 31/12 | (2006.01) |
| A61K 31/675 | (2006.01) |

(52) U.S. Cl.
CPC ........ C07F 9/65616 (2013.01); A61K 31/675 (2013.01); A61P 31/12 (2018.01); A61P 31/18 (2018.01); A61P 31/20 (2018.01); C07F 9/6561 (2013.01)

(58) Field of Classification Search
CPC ...... C07F 9/65616; A61P 31/12; A61P 31/20; A61P 31/18
USPC .......................................................... 514/81
See application file for complete search history.

(56) References Cited

U.S. PATENT DOCUMENTS

2013/0210757 A1    8/2013  Huang et al.

FOREIGN PATENT DOCUMENTS

| CN | 1443189 A | 9/2003 |
|---|---|---|
| CN | 103435672 A | 12/2013 |
| CN | 103980318 A | 8/2014 |
| CN | 104640444 A | 5/2015 |
| WO | WO 2002/008241 A2 | 1/2002 |
| WO | WO 2009/005693 A1 | 1/2009 |

OTHER PUBLICATIONS

International Patent Application No. PCT/CN2016/083407; Int'l Written Opinion and Search Report; dated Sep. 7, 2016; 8 pages.
Lee et al.; "Selective Intracellular Activation of Novel Prodrug of the Human Immunodeficiency Virus Reverse Transcriptase Inhibitor Tenofovir Leads to Preferential Distribution and Accumulation in Lymphatic Tissue"; Antimicrobial Agents and Chemotherapy; vol. 49 No. 5; May 2005; p. 1898-1906.

*Primary Examiner* — Kristin A Vajda
(74) *Attorney, Agent, or Firm* — Baker & Hostetler LLP

(57) ABSTRACT

The present invention relates to a tenofovir monobenzyl ester phosphamide prodrug, preparation method and pharmaceutical use thereof. Specifically, the present invention relates to a compound of general formula (X), or isomer, pharmaceutically-acceptable salt, hydrate or solvate thereof, preparation method and use thereof in the preparation of drugs for treating viral infectious diseases, preferably AIDS infection, hepatitis B or diseases caused by hepatitis B virus.

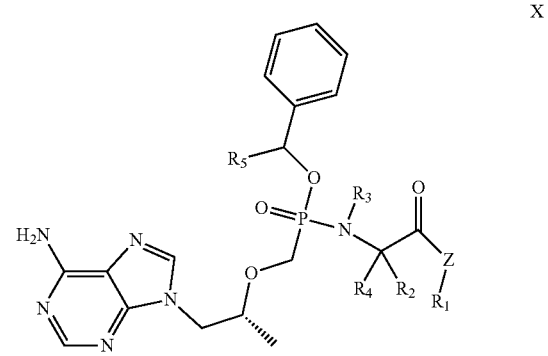

20 Claims, No Drawings

TENOFOVIR MONOBENZYL ESTER PHOSPHAMIDE PRODRUG, PREPARATION METHOD AND USE THEREOF

CROSS-REFERENCE TO RELATED APPLICATIONS

This application is the National Stage of International Application No. PCT/CN2016/083407, filed May 26, 2016, which claims the benefit of Chinese application number 201510290530.9 filed May 29, 2015 the disclosures of which are incorporated herein by reference in their entireties.

TECHNICAL FIELD

The present invention belongs to the field of medicinal chemistry, and specifically relates to a novel tenofovir monobenzyl ester phosphamide compound, or the hydrate, solvate, pharmaceutically acceptable salt or single chiral isomer thereof, as well as the preparation method thereof and use thereof in the medicine.

BACKGROUND ART

Tenofovir Disoproxil Fumarate (TDF) is a water soluble anti-HIV and anti-HBV oral drug, stable in the stomach, enters the body with the blood after the intestinal absorption, and uniformly distributed within human tissues; less than 20% is metabolized and activated into the Tenofovir parent drug under the action of esterase, and then diphosphorylated into Tenofovir diphosphate to take effect, and about the remaining 80% is excreted out of the body in original form. To improve the bio-availability, currently, the strategy of introducing the masking group onto the phosphate group of the Tenofovir to form the lipid soluble pro-drug is usually adopted. Structurally, one masking group is linked with the phosphate group to form a phosphoramide structure, another group linked with the phosphate group to form a phospholipid structure. The compound with this structure is proven to have the lymph and liver tissue targeting effect. Ester-forming groups include various aromatic rings and heteroaromatic rings, especially the substituted or unsubstituted phenyl (CN201310041647.4, WO 200208241 A2). The patent (CN01813161) disclosed a compound GS-7340 obtained by using such pro-drug strategy, which enhanced the liver-targeting properties compared with Tenofovir Disoproxil Fumarate (TDF), while the efficacy enhanced and the toxicity reduced. However, due to the unstability of the phenol group acting as the masking group, metabolism may still occur in the blood to produce the active parent drug Tenofovir, and therefore brings certain systemic toxicity. The phenol produced by the metabolism also has relatively high toxicity itself. The benzyl type Tenofovir pro-drug compound with substitution(s) on the benzene ring has been proven to have liver-targeting activities. Patents US20130210757 and CN201380030061.6 disclosed that one masking group was phosphoramide formed by the amino acid ester and the phosphate group; another masking group was benzyl ester with substitution(s) on the benzene ring formed by benzyl with the electron-donating groups such as methyl on the benzene ring at the ortho or para position, and the phosphate group. However, there's no report of the synthesis and bio-activity researches for the Tenofovir pro-drug compound by using the unsubstituted benzyl as an ester-forming group, in part because the benzyl group without substitution(s) on the benzene ring can not be metabolized during the use of the 5-fluorouracil nucleotide pro-drug, causing it to be not active (WO 200208241 A2).

The masking group of o-methyl benzyl of the compound structure disclosed in CN201380030061.6 has a high group-leaving activity and low stability during the blood esterase metabolism, the targeting group is relatively easier to be detached, therefore leading to the relative increase of the active parent drug in the blood and relative decrease of the active parent drug in the liver, and affecting the activity and systemic toxicity.

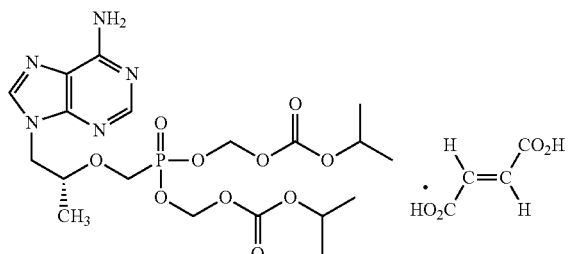

TDF

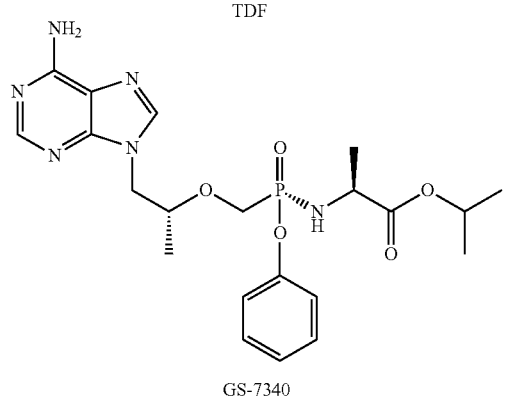

GS-7340

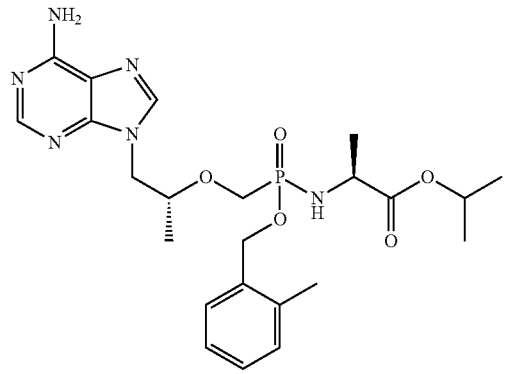

CN201380030061.6

To enhance the bio-activity of Tenofovir and upgrade its anti-virus activity, the present invention provides a class of tenofovir monobenzyl ester phosphamide compounds without substitution(s) on the benzene ring of the benzyl group, and the preparation method thereof, as well as their use in the lymph-targeting anti-AIDS infection and the liver-targeting anti-hepatitis B treatment; compared with GS-7340 and compound 7, such pro-drugs are more stable against esterase, and further enhance the systemic stability and liver-targeting anti-virus effect of the Tenofovir analogs.

SUMMARY OF THE INVENTION

The inventors of the present invention invented a class of tenofovir monobenzyl ester phosphamide compounds, and accidentally found that the compounds of the present invention can be metabolized into the active parent drug of Tenofovir (TFV) in the cell test, and therefore have anti-virus activities. In the in vivo animal test, after gastric gavage to the mice, the compounds can be enriched in the liver, where they are metabolized into the active product of Tenofovir. Compared with the prior art, the compounds of the present invention have a higher anti-HBV activity, or are more stable in the plasma, their metabolic segments are safer, and therefore the systemic toxic and side effects caused by the plasma metabolism are reduced.

In particular, the present invention provides a tenofovir monobenzyl ester phosphamide compound of the general formula X, and the hydrate, solvate, pharmaceutically acceptable salt thereof or the resolved single isomer thereof.

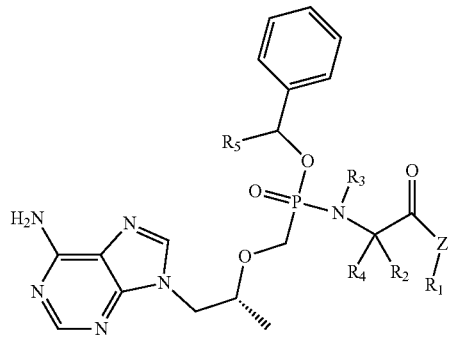

X wherein Z is selected from O, S, Se, NH— or CH2—, $R_1$, $R_2$, $R_3$, $R_4$, and $R_5$ are each independently selected from H, substituted or unsubstituted $C_1$-$C_{10}$ linear alkyl, $C_3$-$C_{10}$ branched alkyl, $C_3$-$C_{10}$ cycloalkyl, and $C_6$-$C_{10}$ aryl or heteroaryl, wherein the substitution is one to three hetero atoms independently selected from O, S, N and Se, or a substituted or unsubstituted 3-8 membered ring formed by $R_1$ and $R_2$, $R_1$ and $R_3$, or $R_2$ and $R_3$ with the moiety they are attached to.

Preferably,

Z is selected from O or S, $R_1$, $R_2$, $R_3$, $R_4$ and $R_5$ are each independently selected from H, substituted or unsubstituted $C_1$-$C_6$ linear alkyl, $C_3$-$C_6$ branched alkyl, $C_3$-$C_6$ cycloalkyl, and $C_6$-$C_{10}$ aryl or heteroaryl.

More preferably,

Z is selected from O, $R_1$, $R_2$, $R_3$, $R_4$ and $R_5$ are each independently selected from H, substituted or unsubstituted $C_1$-$C_6$ linear alkyl, $C_3$-$C_6$ branched alkyl, and $C_6$-$C_{10}$ aryl.

Preferably, the tenofovir monobenzyl ester phosphamide compounds of the present invention are selected from the compounds in Table 1.

TABLE 1

| Compounds and the structures | |
|---|---|
| Compound Name | Structure |
| Compound 1 | (structure 1) |
| Compound 2 | (structure 2) |

TABLE 1-continued
Compounds and the structures
| Compound Name | Structure |
|---|---|
| Compound 3 | 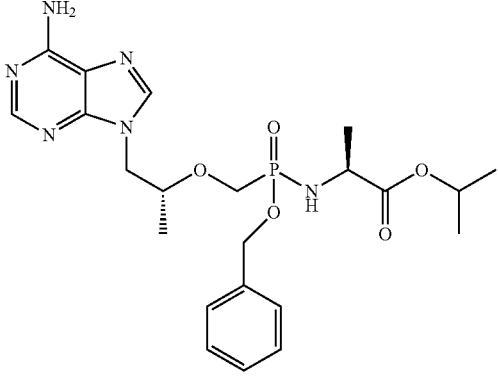 |
| Compound 4 | 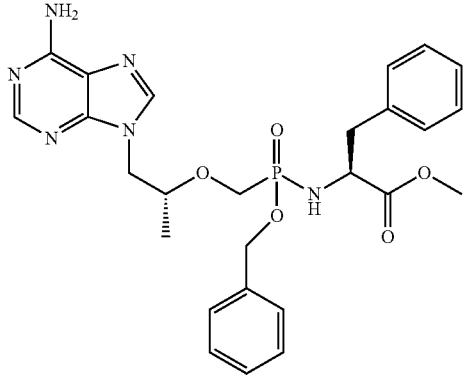 |
| Compound 5 | 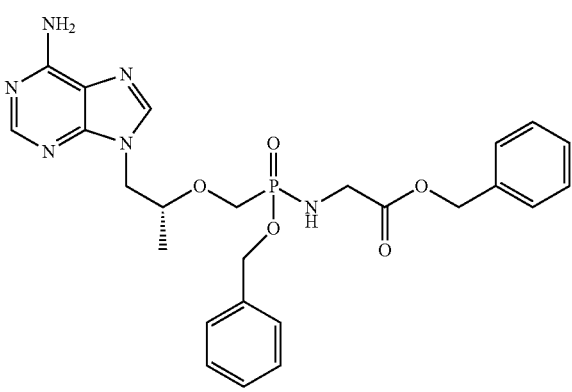 |

TABLE 1-continued

Compounds and the structures

| Compound Name | Structure |
|---|---|
| Compound 6 | 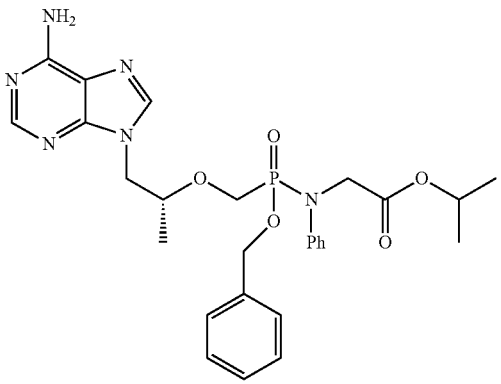<br>6 |

We found that the stereochemistry of the pro-drug can affect its metabolic ability and anti-virus activity in the targeting tissues, and the chiral moiety is on the phosphorus atom, and is also found to be on its masking group of amino acid. For example, amino acids with natural configurations have better metabolic activities, and the S isomer of compound 3 with the configuration of the P atom has a higher activity. If the chiral sites are not pure, these diastereomers or racemates need be chirally enriched so that the screened result makes more sense. The isomer with a single configuration at the chiral center described above is obtained through purification by chiral resolution so that each test compound is essentially a compound with the single chirality. Formation of the essentially single compound or chiral enrichment means that the stereoisomer in need accounts for more than about 60%, usually more than 80%, and preferably more than 95% of the compound by weight. The separation is carried out through the reverse chromatography column or the chiral chromatography column in the present invention, and the mobile phase is aqueous acetonitrile solution.

Another objective of the present invention is to provide a preparation method of the tenofovir monobenzyl ester phosphamide compound, characterized in that the method includes the following steps:

A: Tenofovir is reacted with benzyl halide or benzyl alcohol in the presence of bases to produce the intermediate of the tenofovir monobenzyl ester.

B: The intermediate of the tenofovir monobenzyl ester is reacted with various compounds containing terminal NH groups to produce the tenofovir monobenzyl ester phosphamide compound of the present invention.

Wherein, in step A, Tenofovir is preferably reacted with benzyl bromide or benzyl alcohol, and the base can be various inorganic or organic bases, preferably the organic bases; in step B, the compounds containing the terminal NH group are preferably amino acid ester compounds or amino acid amide compounds.

In particular, sequentially adding di-isopropyl ethyl amine (DIPEA), benzyl bromide or benzyl alcohol into a suspension of Tenofovir in acetonitrile, heating this mixture to 50° C.-80° C. and heat-preservation stirring for 2-24 hours, adding pyridine and dissolving, and then sequentially adding triethyl amine and any one of benzyl glycine ester hydrochlorate, methyl glycine ester hydrochlorate, isopropyl L-alanine ester hydrochlorate, isopropyl L-phenylalanine ester hydrochlorate, isopropyl glycine ester hydrochlorate, and isopropyl N-phenyl glycine ester hydrochlorate, heating the mixture to 50° C.-80° C. and stirring for 10-60 minutes, adding triphenyl phosphine and 2,2'-dithiodipyridine at this temperature, stirring for 3 hours under the temperature of 50° C.-100° C., and then spinning to dryness under reduced pressure. Passing the residues through a silica gel column (eluted by methanol/methylene chloride) to obtain a white solid product.

The synthetic route is present as follow:

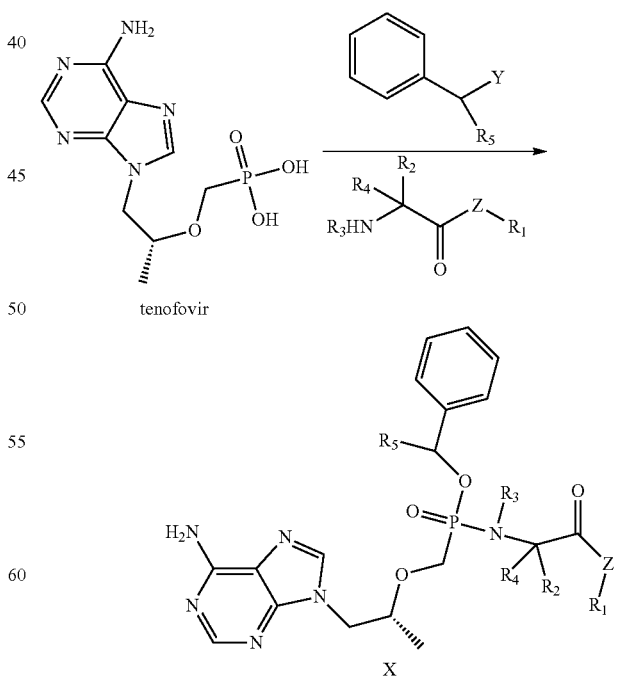

The present invention further includes the chiral resolution method of the compound; collecting eluents of different retention times of the HPLC preparation column separation (preparation column: C18, mobile phase: 10%-50% aqueous acetonitrile solution (V/V)) or the chiral column separation, drying to obtain the isomers of different chiralities.

The present invention also provides a pharmaceutical composition comprising the tenofovir monobenzyl ester phosphamide compound, or the hydrate thereof, or the solvate thereof, or the pharmaceutically acceptable salt thereof or the resolved single isomer thereof.

As desired, conventional techniques in the field of chemistry can be used, and the pharmaceutically acceptable salt of the compound of the present invention can be obtained by the way of acid-base neutralization. For example, let the compound of the present invention react with sulfuric acid, hydrochloric acid, hydrobromic acid, phosphoric acid, tartaric acid, fumaric acid, maleic acid, citric acid, acetic acid, formic acid, methanesulfonic acid, toluenesulfonic acid, oxalic acid or succinic acid to obtain the corresponding salt. Or let the compound of the present invention react with sodium hydroxide, potassium hydroxide, barium hydroxide, etc., an alkali carbonate such as sodium carbonate and calcium carbonate etc., to obtain the corresponding salt. The reaction can be carried out in a solvent such as water or an organic solvent such as ethanol, tetrahydrofuran, dioxane, ethylene glycol, and acetic acid, etc., or the mixture of such organic solvent and water. If required, the reaction can also be carried out without any solvent.

The pharmaceutical composition of the present invention, preferably in unit dosage form of pharmaceutical preparation, can be made into any pharmaceutically acceptable dosage forms during the pharmaceutical preparation; these dosage forms are selected from: tablets, sugar coated tablets, film coated tablets, enteric coated tablets, capsules, hard capsules, soft capsules, oral liquid, oral agents, granules, suspensions, solutions, injections, suppositories, ointments, emplastrums, creams, sprays and patches, preferably oral preparations, and most preferably tablets and capsules. Furthermore, the pharmaceutical composition described in the present invention also comprises a pharmaceutically acceptable carrier.

Conventional techniques of the pharmaceutics can be used to prepare the pharmaceutical preparation, for example, mixing the tenofovir monobenzyl ester phosphamide compound of the present invention, or the hydrate thereof, or the solvate thereof, or the pharmaceutically acceptable salt thereof or the resolved single isomer thereof with a pharmaceutically acceptable carrier. The pharmaceutically acceptable carrier includes, but is not limited to, mannitol, sorbitol, sorbic acid or the potassium salt thereof, sodium metabisulfite, sodium bisulfite, sodium thiosulfate, cysteine hydrochloride, thioglycolic acid, methionine, vitamin A, vitamin C, vitamin E, vitamin D, azone, EDTA disodium, EDTA calcium sodium, carbonate, acetate, phosphate of monovalent alkali metal or the aqueous solution thereof, hydrochloride acid, acetic acid, sulfuric acid, phosphoric acid, amino acid, fumaric acid, sodium chloride, potassium chloride, sodium lactate, xylitol, maltose, glucose, fructose, dextran, glycine, starch, sucrose, lactose, mannitol, silicon derivatives, cellulose and derivatives thereof, alginate, gelatin, polyvinylpyrrolidone, glycerol, propylene glycol, ethanol, tween 60-80, span-80, bees wax, lanolin, liquid paraffin, cetyl alcohol, gallic acid ester, agar, triethanolamine, basic amino acid, urea, glyoxyldiureide, calcium carbonate, calcium bicarbonate, surfactant, polyethylene glycol, cyclodextrin, β-cyclodextrin, phospholipid materials, kaolin, talc, calcium stearate, and magnesium stearate, etc.

When the pharmaceutical composition of the present invention is made into preparations, unit dosage form can contain 0.1-1000 mg of the pharmaceutically active substance of the present invention, and the balanced is pharmaceutically acceptable carrier. Pharmaceutically acceptable carriers account for 0.1-99.9% of total weight of the preparations by weight.

The usage and dosage of the pharmaceutical compositions of the present invention are determined according to patients' conditions while being used.

The present invention finally also provides a use of the tenofovir monobenzyl ester phosphamide compound, or the hydrate thereof, or the solvate thereof, or the pharmaceutically acceptable salt thereof or the resolved single isomer thereof in the preparation of the drugs for treating viral infection diseases, preferably the use in the preparation of drugs for treating AIDS infection or hepatitis B or diseases caused by the hepatitis B virus.

DETAILED DESCRIPTION OF THE INVENTION

The present invention will be explained in detail below with reference to the specific examples, so that those skilled in the art can have a more comprehensive understanding of the present invention. The specific examples are used only for the illustration of the technical solution of the present invention, and not in any way for the limitation of the present invention.

Embodiment 1: Preparation of Compound 1

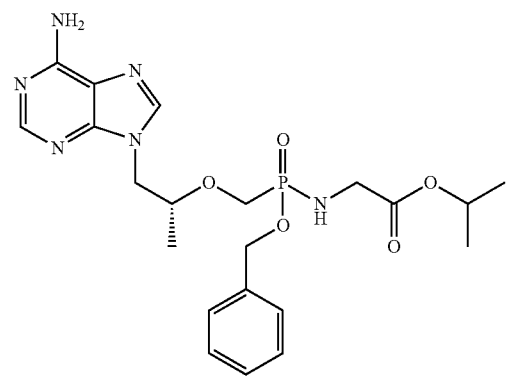

DIPEA (10 mmol) and benzyl bromide (5 mmol) were added into the suspension of Tenofovir (5 mmol) in acetonitrile (20 mL) sequentially, the mixture was heated to 80° C. and stirred for 16 hours and then evaporated to dryness under reduced pressure. The residues were dissolved with pyridine (20 mL), then triethylamine (5 mL) and isopropyl glycine ester hydrochlorate (10 mmol) were added to the solution sequentially. The mixture was heated to 50° C. and stirred for 30 minutes, then after triphenyl phosphine (15 mmol) and 2,2'-dithiodipyridine (15 mmol) were added, stirred for 3 hours under the same temperature, and evaporated to dryness under reduced pressure thereafter. The residues were subjected to a silica gel column (eluted by methanol/methylene chloride) to afford a white solid. The yield was 48%.

$^1$H NMR (400 MHz, CDCl$_3$) δ 8.30 (s, 1 H), 7.94, 7.91 (s, s, 1H), 7.37-7.28 (m, 5 H), 6.10, 6.07 (s, s, 2 H), 5.07-4.89 (m, 3 H), 4.38-4.30 (m, 1 H), 4.14-4.05 (m, 1 H), 3.91-3.86 (m, 2 H), 3.71-3.48 (m, 4 H), 1.25-1.18(m, 9 H);

$^{31}$P NMR (400 MHz, CDCl$_3$) δ 25.76, 25.66; MS (m/z) 477.32 (MH$^+$), 475.18 (MH$^-$).

Embodiment 2: Preparation of Compound 2

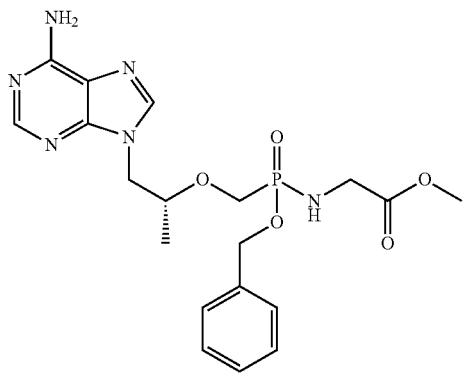

2

DIPEA (10 mmol) and benzyl bromide (5 mmol) were added into the suspension of Tenofovir (5 mmol) in acetonitrile (20 mL) sequentially, the mixture was heated to 80° C. and stirred for 16 hours and then evaporated to dryness under reduced pressure. The residues were dissolved with pyridine (20 mL), then triethylamine (5 mL) and methyl glycine ester hydrochlorate (10 mmol) were added to the solution sequentially. The mixture was heated to 50° C. and stirred for 30 minutes, then triphenyl phosphine (15 mmol) and 2,2'-dithiodipyridine (15 mmol) were added, stirred for 3 hours under the same temperature, and evaporated to dryness under reduced pressure thereafter. The residues were subjected to a silica gel column (eluted by methanol/methylene chloride) to afford a white solid. The yield was 57%.

$^1$H NMR (400 MHz, CDCl$_3$) δ 8.26 (s, 1 H), 7.93, 7.92 (s, s, 1 H), 7.31-7.4 (m, 5 H), 6.37 (s, 2 H), 5.01-4.86 (m, 2 H), 4.33-4.25 (m, 1 H), 4.10-4.01 (m, 1 H), 3.93-3.80 (m, 2 H), 3.67-3.53 (m, 4 H), 1.40-1.14 (m, 6 H); $^{31}$P NMR (400 MHz, CDCl$_3$) δ 25.96, 25.73; MS (m/z) 449.30 (MH$^+$).

Embodiment 3: Preparation of Compound 3

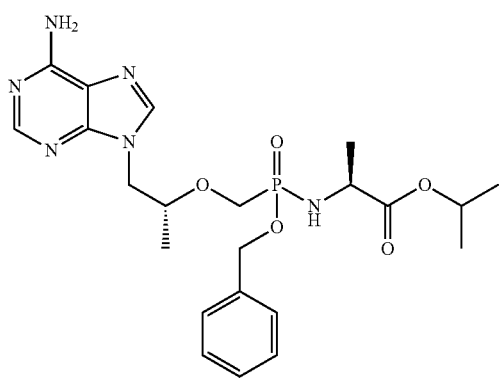

3

DIPEA (10 mmol) and benzyl bromide (5 mmol) were added into the suspension of Tenofovir (5 mmol) in acetonitrile (20 mL) sequentially, the mixture was heated to 80° C. and stirred for 16 hours and then evaporated to dryness under reduced pressure. The residues were dissolved with pyridine (20 mL), then triethylamine (5 mL) and isopropyl L-alanine ester hydrochlorate (10 mmol) were added to the solution sequentially. The mixture was heated to 50° C. and stirred for 30 minutes, then after triphenyl phosphine (15 mmol) and 2,2'-dithiodipyridine (15 mmol) were added, stirred for 3 hours under the same temperature, and evaporated to dryness under reduced pressure thereafter. The residues were subjected to a silica gel column (eluted by methanol/methylene chloride) to afford a white solid. The yield was 54%.

$^1$H NMR (400 MHz, CDCl$_3$) δ 8.34, 8.33 (s, s, 1 H), 7.93, 7.92 (s, s, 1 H), 7.36-7.30 (m, 5 H), 6.00, 5.99 (s, s, 2 H), 5.06-4.97 (m, 2 H), 4.94-4.89 (m, 1 H), 4.40-4.28 (m, 1 H), 4.14-4.06 (m, 1 H), 4.03-3.92 (m, 2 H), 3.89-3.78 (m, 2 H), 3.67-3.53 (m, 2 H), 1.33-1.18 (m, 12 H); $^{31}$P NMR (400 MHz, CDCl$_3$) δ 25.02, 24.12; MS (m/z) 491.32 (MH$^+$).

Embodiment 4: Preparation of Compound 4

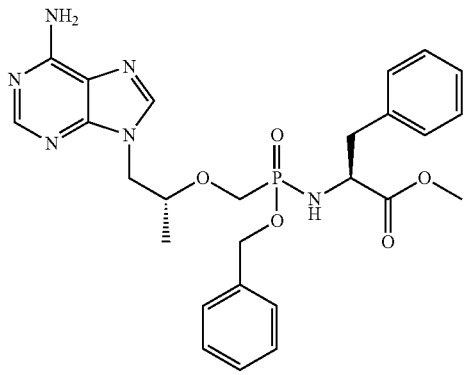

4

DIPEA (10 mmol) and benzyl bromide (5 mmol) were added into the suspension of Tenofovir (5 mmol) in acetonitrile (20 mL) sequentially, the mixture was heated to 80° C. and stirred for 16 hours and then evaporated to dryness under reduced pressure. The residue was dissolved with pyridine (20 mL), then triethylamine (5 mL) and L-Phenylalanine isopropyl ester hydrochloride (10 mmol) were added to the solution sequentially. The mixture was heated to 50° C. and stirred for 30 minutes, then after triphenyl phosphine (15 mmol) and 2,2'-dithiodipyridine (15 mmol) were added, stirred for 3 hours under the same temperature, and evaporated to dryness under reduced pressure thereafter. The residues were subjected to a silica gel column (eluted by methanol/methylene chloride) to afford a white solid. The yield was 61%.

$^1$H NMR (400 MHz, CDCl$_3$) δ 8.33 (s, 1 H), 7.90 (s, 1 H), 7.30-7.09 (m, 10 H), 6.23 (s, 2 H), 5.03-4.88 (m, 2 H), 4.33-4.29 (m, 1 H), 4.15-3.90 (m, 3 H), 3.81-3.71 (m, 1 H), 3.48-3.43 (m, 1 H), 3.21-3.02 (m, 3 H), 2.94-2.76 (m, 2 H), 1.47-1.42(m, 3 H), 1.26-1.07 (m, 9 H); $^{31}$P NMR (400 MHz, CDCl$_3$) δ 20.78; MS (m/z) 567.32 (MH$^+$).

Embodiment 5: Preparation of Compound 5

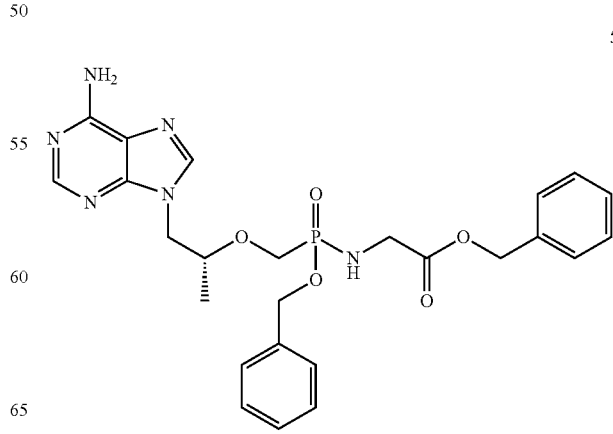

5

DIPEA (10 mmol) and benzyl bromide (5 mmol) were added into the suspension of Tenofovir (5 mmol) in acetonitrile (20 mL) sequentially, the mixture was heated to 80° C. and stirred for 16 hours and then evaporated to dryness under reduced pressure. The residues were dissolved with pyridine (20 mL), then triethylamine (5 mL) and benzyl glycine ester hydrochlorate (10 mmol) were added to the solution sequentially. The mixture was heated to 50° C. and stirred for 30 minutes, then after triphenyl phosphine (15 mmol) and 2,2'-dithiodipyridine (15 mmol) were added, the mixture was stirred for 3 hours under the same temperature, and evaporated to dryness under reduced pressure thereafter. The residues were subjected to a silica gel column (eluted by methanol/methylene chloride) to afford a white solid. The yield was 58%.

$^1$H NMR (400 MHz, CDCl$_3$) δ 8.30, 8.29 (s, s, 1 H), 7.93, 7.92 (s, s, 1 H), 7.37-7.27 (m, 10 H), 6.14 (s, 2 H), 5.31 (s, 1 H), 5.15 (s, 1 H), 5.10 (s, 1 H), 5.04-4.87 (m, 2 H), 4.34-4.26 (m, 1 H), 4.09-4.00 (m, 1 H), 3.92-3.81 (m, 2 H), 3.76-3.54 (m, 1 H), 3.17-3.11 (m, 2 H), 1.18-1.16 (m, 3 H); $^{31}$P NMR (400 MHz, CDCl$_3$) δ 25.81, 25.61; MS (m/z) 525.19 (MH$^+$).

Embodiment 6: Preparation of Compound 6

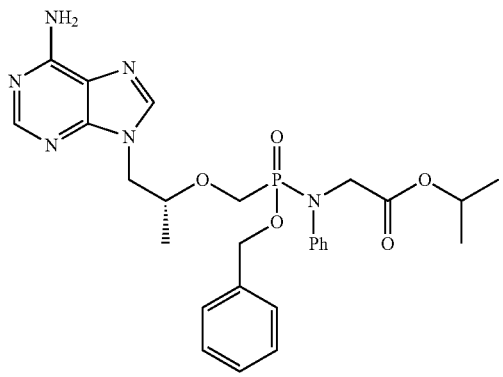

6

DIPEA (10 mmol) and benzyl bromide (5 mmol) were added into the suspension of Tenofovir (5 mmol) in acetonitrile (20 mL) sequentially, the mixture was heated to 80° C. and stirred for 16 hours and then evaporated to dryness under reduced pressure. The residues were dissolved with pyridine (20 mL), then triethylamine (5 mL) and isopropyl N-phenylglycine ester hydrochlorate (10 mmol) were added to the solution sequentially. The mixture was heated to 50° C. and stirred for 30 minutes, then after triphenyl phosphine (15 mmol) and 2,2'-dithiodipyridine (15 mmol) were added, the mixture was stirred for 3 hours under the same temperature, and evaporated to dryness under reduced pressure thereafter. The residues were subjected to a silica gel column (eluted by methanol/methylene chloride) to afford a white solid. The yield was 27%.

$^1$H NMR (400 MHz, CDCl$_3$) δ 8.29 (s, 1 H), 8.09 (s, 1 H), 7.50-7.14 (m, 10 H), 6.60 (s, 2 H), 5.07-4.90 (m, 3 H), 4.37-4.34 (m, 7 H), 3.17-3.12 (m, 3 H), 1.45-1.41 (m, 6 H); $^{31}$P NMR (400 MHz, CDCl$_3$) δ 24.43, 24.15; MS (m/z) 553.25 (MH$^+$).

Embodiment 7: Preparation of the Compounds Through Chiral Resolution

Resolution via HPLC with reverse phase column or chiral column: compound 2 (200 mg) of embodiment 2 was chiral resolved by HPLC with reverse phase column (column: Diamonsil C18, 5 μm, 150×21.1 mm; mobile phase: 20% aqueous acetonitrile solution (V/V)), afforded compound 2a (83 mg; retention time: 14 min) and compound 2b (90 mg; retention time: 17 min).

Compound 2a: MS (m/z) 449.26 (MH$^+$); $^1$H NMR (400 MHz, CDCl$_3$) δ 8.28 (s, 1 H), 7.92 (s, 1 H), 7.32-7.24 (m, 5 H), 6.58 (s, 2 H), 5.02-4.88 (m, 2 H), 4.30-4.26 (m, 1 H), 4.16-4.02 (m, 1 H), 3.90-3.84 (m, 2 H), 3.69-3.65 (m, 5 H), 3.60-3.54 (m, 1 H), 1.16 (s, 3 H); $^{31}$P NMR (400 MHz, CDCl$_3$) δ 25.87;

Compound 2b: MS (m/z) 449.32 (MH$^+$); $^1$H NMR (400 MHz, CDCl$_3$) δ 8.28 (s, 1 H), 7.92 (s, 1 H), 7.32-7.27 (m, 5 H), 6.64 (s, 2 H), 5.03-5.01 (m, 2 H), 4.34-4.30 (m, 1 H), 4.10-4.01 (m, 2 H), 3.93-3.84 (m, 2 H), 3.66-3.59 (m, 5 H), 1.14 (s, 3 H); $^{31}$P NMR (400 MHz, CDCl$_3$) δ 25.64.

Similar resolution was applied to compounds 1, 3 and 5, and afforded compounds 1a and 1b, 3a and 3b, 5a and 5b respectively.

Compound 1a: $^1$H NMR (400 MHz, CDCl$_3$) δ 8.25 (s, 1 H), 7.93 (s, 1 H), 7.30-7.26 (m, 5 H), 6.17 (s, 2 H), 5.00-4.90 (m, 2 H), 4.34-4.29 (m, 1 H), 4.11-4.06 (m, 2 H), 3.92-3.81 (m, 2 H), 3.63-3.59 (m, 3 H), 1.18-1.23 (m, 9 H); $^{31}$P NMR (400 MHz, CDCl$_3$) δ 25.79;

Compound 1b: $^1$H NMR (400 MHz, CDCl$_3$) δ 8.28 (s, 1 H), 7.92 (s, 1H), 7.32-7.27 (m, 5H), 6.64 (s, 2 H), 5.03-5.01 (m, 2 H), 4.34-4.30 (m, 1 H), 4.10-4.01 (m, 2 H), 3.93-3.84 (m, 2 H), 3.66-3.59 (m, 3 H), 1.16-1.14 (m, 9 H); $^{31}$P NMR (400 MHz, CDCl$_3$) δ 25.60.

Compound 3a: $^1$H NMR (400 MHz, CDCl$_3$) δ 8.30 (s, 1 H), 7.90 (s, 1 H), 7.32-7.27 (m, 5 H), 6.19 (s, 2 H), 5.03-4.96 (m, 2 H), 4.92-4.87 (m, 1 H), 4.30-4.25 (m, 1 H), 4.09-4.03 (m, 1 H), 3.97-3.94 (m, 1 H), 3.90-3.76 (m, 2 H), 3.56-3.50 (m, 1 H), 1.30-1.15 (m, 12 H); $^{31}$P NMR (400 MHz, CDCl$_3$) δ 24.18;

Compound 3b: $^1$H NMR (400 MHz, CDCl$_3$) δ 8.30 (s, 1 H), 7.91 (s, 1 H), 7.36-7.29 (m, 5 H), 6.09 (s, 2 H), 4.99-4.96 (m, 2 H), 4.94-4.87 (m, 1 H), 4.38-4.34 (m, 1 H), 4.12-4.06 (m, 1 H), 3.96-3.90 (m, 2 H), 3.87-3.81 (m, 1 H), 3.60-3.55 (m, 1 H), 3.45-3.40 (m, 1H), 1.31-1.16 (m, 12 H); $^{31}$P NMR (400 MHz, CDCl$_3$) δ 25.04

Compound 5a: $^1$H NMR (400 MHz, CDCl$_3$) δ 8.28 (s, 1 H), 7.95 (s, 1 H), 7.40-7.23 (m, 10 H), 6.33 (s, 2 H), 5.10-4.95 (m, 4 H), 4.32-4.28 (m, 1 H), 4.01-3.84 (m, 2 H), 3.82-3.55 (m, 4 H), 1.24 (s, 3 H); $^{31}$P NMR (400 MHz, CDCl$_3$) δ 25.88

Compound 5b: $^1$H NMR (400 MHz, CDCl$_3$) δ; 8.27 (s, 1 H), 7.94 (s, 1 H), 7.34-7.27 (m, 10 H), 6.12 (s, 2 H), 4.96-4.84 (m, 4 H), 4.28-4.23 (m, 1 H), 3.83-3.51 (m, 6 H), 1.15 (s, 3 H); $^{31}$P NMR (400 MHz, CDCl$_3$) δ 25.59

TABLE 2

List of the chiral compounds of the present invention

| Compound | Structure |
|---|---|
| 1a | (structure shown) |

TABLE 2-continued

List of the chiral compounds of the present invention

| Compound | Structure |
|---|---|
| 1b | *(structure 1b)* |
| 2a | *(structure 2a)* |
| 2b | *(structure 2b)* |
| 3a | *(structure 3a)* |
| 3b | *(structure 3b)* |
| 5a | *(structure 5a)* |
| 5b | *(structure 5b)* |

In the above compounds, each of the configurations a and b accounts for 50% of the compounds.

Embodiment 8

The mixture of one chiral compound of embodiment 7 in Table 2 (1.2 kg), fumaric acid (285 g), and acetonitrile (3 L) was refluxed until it turned to homogeneous and then was filtered while hot. the filtrate was cooled to 5° C. and kept for 16 hours at the same temperature. The precipitate was filtered and washed with acetonitrile, dried to afford the product as white powder.

Test examples: The advantage of the present invention is demonstrated by the test examples described below.

The most crucial profile of a prodrug is that it is apt to metabolite to the active parent drug meanwhile maintain unattached in other systems, that is, the more stable in systems (gastrointestinal tract, blood, etc.), and more active in the target organs (lymph, liver), then it will be more effective and less toxic as a drug candidate. In the test examples, all the prodrugs, including compounds in the present invention and in the reference, will play their anti-virus effect after being metabolized into Tenofovir (TFV), the active parent drug.

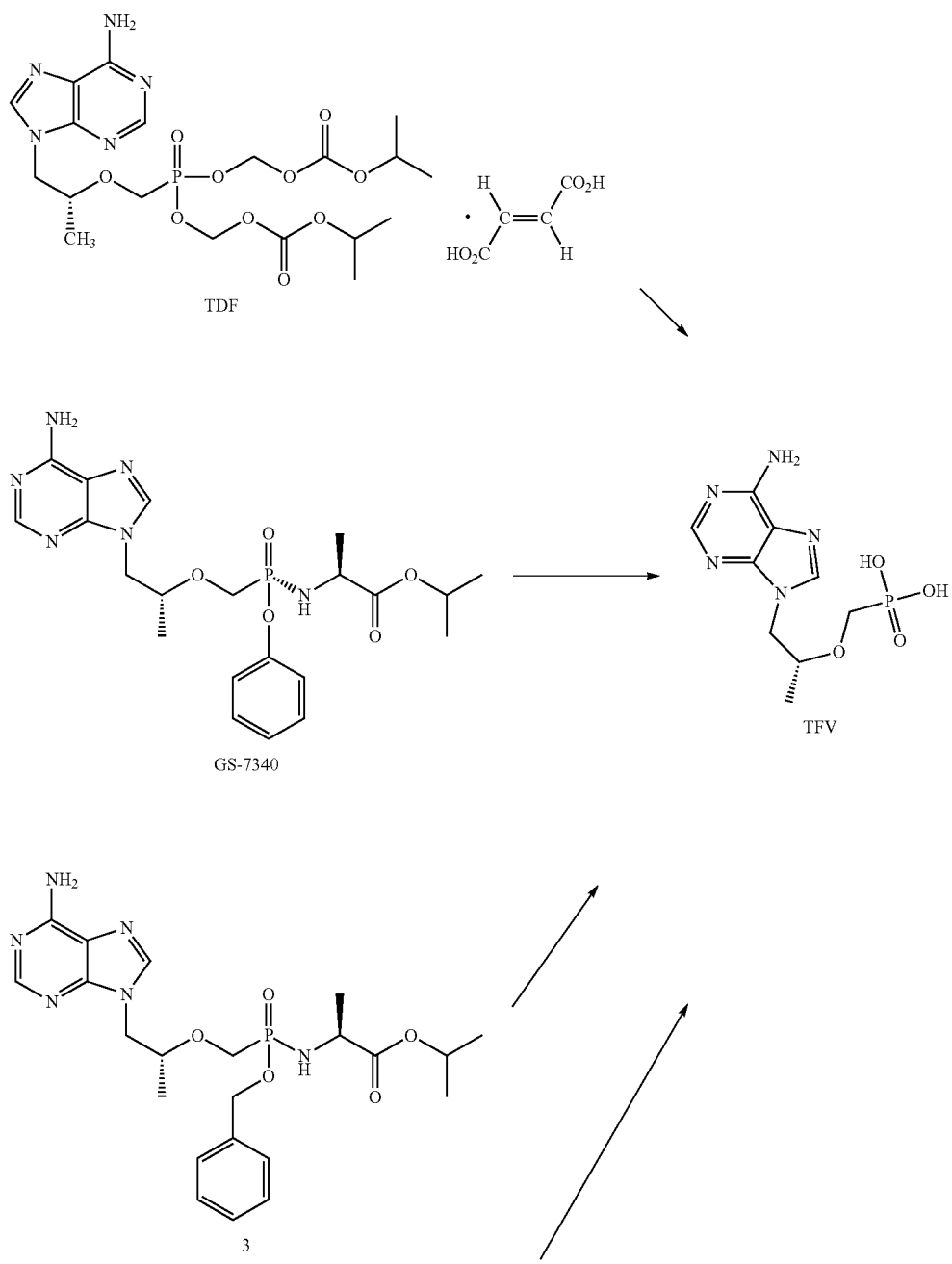

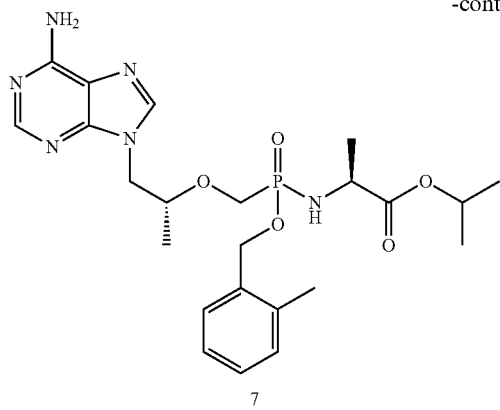

7

Currently, compounds with similar structures are the compounds listed in the claims of patent CN201380030061.6 (abbreviation: compound 7 and its single chiral isomer 7a and 7b thereof), and the drug TAF (GS-7340) for treating hepatitis B, that approved by FDA and launched by Gilead very recently. These compounds share the same parent drug motif as the compounds of the present invention, but the liver-targeting segments are different.

Compounds of the present invention are either more efficient or less toxic due to the higher stability of the structures. Moreover, the metabolites of the compounds of the present invention, benzoic acids, are much safer than their counterpart of GS-7340, the toxic phenol, and bring the advantage of being less toxic while having the superior activity. Furthermore, compared with the compounds in the claims of CN201380030061.6, because the liver-targeting group of the compounds of the present invention is benzyl, which is more stable than o-methyl benzyl, and the activity of benzyl to be detached during the esterase metabolism in blood is comparatively low, the active parent drug in the blood is relatively reduced, the active parent drug in the liver is relatively increased, and therefore exhibit the better activity. The toxicity is lower after benzyl is detached from the compound of the present invention, leading to better systemic stability and lower toxicity. They are specifically present as follow:

Test example 1: Cell based anti-HBV activity and cytotoxicity tests

The concentration of HBV DNA in the HepG2.2.15 cell supernatant was detected through the real-time fluorescence quantitative PCR (qPCR) method to determine the anti-HBV activity of the compound in the HepG2.2.15 cells, and the effect of the testing compounds to the HepG2.2.15 cell activity was detected through Cell-titer Blue.

8.1. Dilution of the compounds: the initial concentration of each compound in the in vitro anti-HBV activity test was 1 μM, with 3-fold serial dilution to 8 concentrations; the initial concentration of each compound in the cytotoxicity test was 100 μM, with 3-fold serial dilution to 8 concentrations; DMSO was used for the dilution of the compound mother liquor. The initial concentrations of the reference compound TDF for the anti-HBV activity test in vitro and the cytotoxicity test were all set at 0.2 μM, with 3-fold serial dilution to 8 concentrations.

8.2. Anti-HBV activity test in vitro: the HepG2.2.15 cells were plated in the 96-well plate ($4\times10^4$ cells/well), and cultured overnight at 37° C. in 5% $CO_2$. On second day, fresh culture solutions containing compounds of different concentrations were added to the culture wells. See Table 2 for the compound distribution. On $5^{th}$ day, the used culture solutions in the culture wells were sucked and discarded, and fresh culture solutions containing compounds of different concentrations were added. On $8^{th}$ day, the supernatant in the culture wells was collected for the extraction of HBV DNA in the supernatant. qPCR test was used to detect the concentration of HBV DNA content in the HepG2.2.15 supernatant.

8.3. Treatment of the cells in the cell viability test: the HepG2.2.15 cells were plated in the 96-well plate ($4\times10^4$ cells/well), and cultured overnight at 37° C. in 5% $CO_2$. On $2^{nd}$ day, fresh culture solutions containing compounds of different concentrations were added to the culture wells. See Table 3 for the compound distribution. On $5^{th}$ day, the used culture solutions in the culture wells were sucked and discarded, and fresh culture solutions containing compounds of different concentrations were added. On $8^{th}$ day, Cell-titer Blue agent was added to each well, and the microplate reader was used to detect the fluorescence value of each well.

8.4. Data analysis and calculation of the inhibition percentage and relative cell viability: The inhibition percentage was calculated using the following formula:

% Inh.=[(HBV quantity of DMSO control−HBV quantity of sample)/HBV quantity of DMSO control]×100%

The cell viability percentage was calculated using the following formula:

% cell viability=(fluorescence of sample−fluorescence of medium control)/(fluorescence of DMSO control−fluorescence of medium control)33 100%

The GraphPad Prism software was used to calculate the 50% effective concentration ($EC_{50}$) value and the 50% cytotoxic concentration ($CC_{50}$) value of the compounds.

8.5. Test results and conclusions:

TABLE 3

$EC_{50}$ and $CC_{50}$ values of the anti-HBV test results of the compounds

| Compounds | $EC_{50}$ (nM) | $CC_{50}$ (μM) |
|---|---|---|
| 1a | >1000 | >100 |
| 1b | 290.1 | >100 |

TABLE 3-continued

EC$_{50}$ and CC$_{50}$ values of the anti-HBV test results of the compounds

| Compounds | EC$_{50}$ (nM) | CC$_{50}$ (μM) |
|---|---|---|
| 2a | 418.4 | >100 |
| 2b | >1000 | >100 |
| 3a | 3.39 | >100 |
| 3b | 6 | >100 |
| 5a | 214 | >100 |
| 5b | 847.6 | >100 |

There were totally 8 test compounds in the present test, and the test results were summarized as the following: 2 test compounds of 3a and 3b showed better anti-HBV activities, with EC$_{50}$ values below the 10 nM level, 4 test compounds of 1b, 2a, 5a, and 5b showed lower anti-HBV activities, with EC$_{50}$ values between 200 nM and 1000 nM; EC$_{50}$ values of the anti-HBV activities of the other 2 test compounds of 1a and 2a were higher than the maximum test concentration of 1000 nM.

The structures of compounds 1, 2, 4, 5, and 6 of the present invention were similar to that of compounds 3, therefore they had the similar pharmacodynamic effects.

Test example 2: Comparative tests of the cell-based anti-HBV activity and cytotoxicity 9.1 Drugs: the dilution method and concentrations of compound 3, the reference compound (CN201380030061.6, and the compound shown in claim 36 (abbreviation: compound 7), and the isomer thereof) were the same as those in example 1.

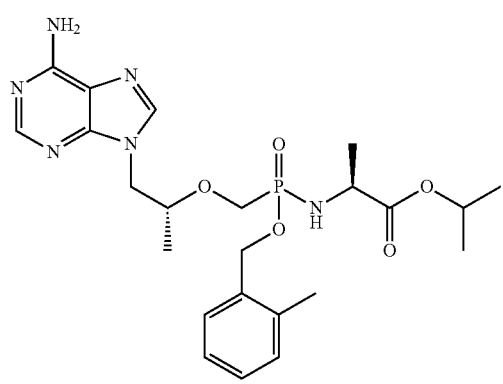

7

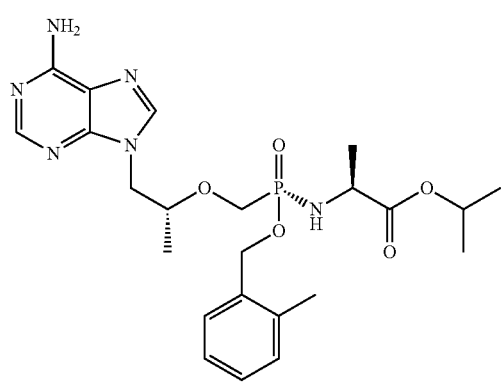

7a

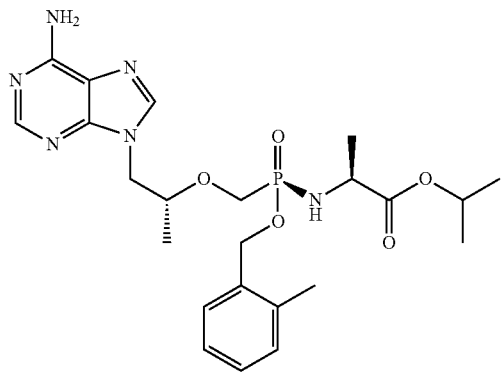

7b

Structures of Compound 7, its Isomers 7a and 7b 9.2 Test method: the test was carried out according to the procedure in example 1.

9.3 Results and analysis:

TABLE 4

EC$_{50}$ and CC$_{50}$ values of the compounds in the anti-HBV test

| Compounds | EC$_{50}$ (nM) | CC$_{50}$ (μM) |
|---|---|---|
| 3a | 3.39 | >100 |
| 3b | 6.00 | >100 |
| 7a | >1000 | >100 |
| 7b | 274.70 | >100 |
| GS-7340 | 17.75 | >100 |

It could be seen from Table 4 that compounds 3a and 3b of the present invention showed good anti-HBV activities, which were significantly better than that of the reference compounds 7a, 7b, and GS-7340. None of the compounds had apparent impact on the cytotoxicity of HepG2.2.15 (CC$_{50}$>100 μM).

Test example 3: Cell based anti-HBV activity and cytotoxicity tests 9.1. Dilution and concentrations of the compounds and the reference compound (CN01813161GS-7340, TDF) were the same as those in example 1.

9.2. In vitro anti-HIV activity test: after MT-4 cells were infected with 24 TCID50HIV-1 IIIB/1×10$^5$ cells (2.4 TCID50/well) at 37° C. for 1 hour, they were plated in the 96-well plate containing the compounds of different concentrations (4×10$^4$ cells/well) and cultured at 37° C. in 5% CO$_2$ for 5 days. CellTiter Glo was used to determine the activity to calculate the EC$_{50}$ value.

9.3. Treatment of the cells in the cell viability test: parallel tests were carried out using the same method as that in 9.2, except that the 96-well plate containing the compounds of different concentrations were replaced with the blank 96-well plate, and CellTiter Glo was used to determine the cell viability to calculate the CC$_{50}$ value.

9.4. Data analysis and calculation of the inhibition percentage: the activity percentage was calculated using the following formula:

Activity (%) =(Raw data$_{cpd}$-Average$_{VC}$)/(Average$_{CC}$-Average$_{VC}$)*100Cell Viability (%)=Raw data$_{cpd}$/Average$_{CC}$*100

The GraphPad Prism software was used to calculate the 50% effective concentration ($EC_{50}$) value and the 50% cytotoxic concentration ($CC_{50}$) value of the compounds.

9.5. Test results and conclusions:

TABLE 5

$EC_{50}$ and $CC_{50}$ values of of the compounds in the anti-HBV test results

| Compounds | $EC_{50}$ (nM) | $CC_{50}$ (μM) |
|---|---|---|
| 3a | 5.13 | 22.53 |
| 3b | 9.86 | 16.89 |
| 7b | 83.65 | 14.72 |
| GS-7340 | 14.28 | 13.34 |
| TDF | 16.97 | 21.33 |

The anti-HIV activities of compounds 3a and 3b were higher than those of 7b and GS-7340; meanwhile the toxicities to the MT-4 cells of 3a and 3b were lower than those of GS-7340 and 7b. Conclusion: it could be seen from example 2 and 3 that, in the preliminary efficacy study, compounds 3a and 3b presented good anti-HBV and anti-HIV activities, and showed significant advantages compared with the activity of GS-7340, the active ingredient of TM. They were apparently superior to the other two control compounds 7a and 7b. Results of the cytotoxicity study: there was no apparent effect on the cytotoxicity of the HepG2.2.15($CC_{50}$>100 μM); however, regarding the toxicity to the MT-4 cells, the data showed that compounds 3a and 3b had lower MT-4 cytotoxicities than GS-7340 and 7b.

Test example 4: Results of the stability study

The following stability test were carried out according to the prior art, and the data of the stability test shown in the table were the residue percentages after the test compounds were incubated for different period of time under the test condition.

TABLE 6

10.1 Stability in the simulated gastric fluid:

| Compounds | % 0 min | % 60 min | % 120 min | % 360 min | % 1440 min |
|---|---|---|---|---|---|
| 3a (10 μM) | 100 | 85.40 | 58.07 | 14.41 | 0.00 |
| 3b (10 μM) | 100 | 84.26 | 58.54 | 17.28 | 0.00 |
| 7b (10 μM) | 100 | 82.76 | 51.39 | 13.16 | 0.00 |
| GS-7340 (10 μM) | 100 | 95.40 | 66.36 | 23.41 | 0.19 |
| (Omeprazole 20 μM) | 100 | 24.34 | 9.41 | 1.58 | 0.31 |

TABLE 7

10.2 Stability in the simulated intestinal fluid (test concentration: 10 μM):

| Compounds | % 0 min | % 60 min | % 120 min | % 360 min | % 1440 min |
|---|---|---|---|---|---|
| 3a | 100 | 53.62 | 23.45 | 1.26 | 0.00 |
| 3b | 100 | 51.07 | 20.20 | 0.23 | 0.00 |
| 7b | 100 | 31.28 | 8.33 | 0.09 | 0.00 |
| GS-7340 | 100 | 30.09 | 6.22 | 0.06 | 0.00 |
| (Chlorambucil) | 100 | 29.36 | 3.11 | 0.00 | 0.00 |

TABLE 8

10.3 Stability in the human blood (test concentration: 2 μM):

| Compounds | % 0 min | % 10 min | % 30 min | % 60 min | % 120 min |
|---|---|---|---|---|---|
| 3a | 100 | 97.4 | 98.9 | 97.8 | 94.5 |
| 3b | 100 | 97.1 | 96.4 | 96.1 | 93.7 |
| 7b | 100 | 93.5 | 91.6 | 90.5 | 90.1 |
| GS-7340 | 100 | 93.2 | 91.0 | 90.3 | 90.0 |
| (Eucatropine) | 100 | 54.4 | 37.0 | 24.4 | 10.2 |

TABLE 9

10.4 Stability in the human liver S9 (test concentration: 1 μM):

| Compounds | $T_{1/2\ min}$ | $CL_{lint(s9)}$ uL/min/mg | $CL_{lint(s9)}$ uL/min/kg | Remaining (T = 60 min) |
|---|---|---|---|---|
| 3a | 9.9 | 70.0 | 246.4 | 6% |
| 3b | 10.1 | 68.6 | 241.5 | 9% |
| 7b | 4.7 | 147.4 | 519.0 | 5% |
| GS-7340 | 3.3 | 211.0 | 742.7 | 4% |
| (7-Ethoxycumarin) | 82.2 | 8.4 | 29.7 | 60% |
| (7-Hydroxycoumarin) | 6.6 | 105.1 | 370.0 | 4% |

The consistency of test results of the related control substances such as 7-Ethoxycumarin, 7-Hydroxycoumarin, Eucatropine, Chlorambucil, and Omeprazole, etc. verified the effectiveness of this set of tests.

10.5 Data analysis and conclusions

The test data of the preliminary stability study showed that, for compounds 3a and 3b, GS-7340 and 7b, the stabilities in the human liver S9 were comparative, also the rates of metabolizing to the active parent drug were comparative, implying that the activities of the compounds of the same concentration in the liver cells were comparative.

In the simulated gastric fluid, the stabilities of 3a and 3b were comparative to GS-7340 but higher than 7b; the stabilities of 3a and 3b in the simulated intestinal fluid were significantly higher than those of 7b and GS-7340. The stabilities of 3a and 3b in the human blood were also better than those of the comparative compounds 7b and GS-7340. Generally, compounds 3a and 3b had higher stabilities in the gastrointestinal tract and blood system compared to GS-7340 and 7b, so that the drug concentration would be lower in the non-target system while higher in the target tissues, implying that compounds 3a and 3b would have better liver-targeting properties and lower systemic toxicities compared to GS-7340 and 7b.

Test example 5: Cardiotoxicity study 11.1. Test cells and compounds preparation

The CHO cells obtained from AVivaBiosciences that could stably express the hERG K-channel were used in the test, and the cells were incubated at 37° C. in 5% $CO_2$ and under constant humidity.

After the compounds and the positive control compound amitriptyline (Amitriptyline, Sigma-Aldrich, BCBJ8594V) were dissolved in 100% dimethyl sulfoxide (DMSO), they were serially diluted and stored at −20° C. for further use. The final concentration of DMSO in the extracellular fluid was not higher than 0.30%.

11.2. The manual patch clamp recording

The whole-cell patch clamp technique was used on the Multiclamp patch-clamp amplifier to test the compound at room temperature, the output signal was digitalized using the DIgiDAta 1440 A/D-D/A plate, and the Pclamp10 software was used for the control of the recording. The minimum sealing resistance was set at 500 MOh/ms, and the minimum specific hERG current was set at 0.4 nA for quality control.

11.3 Data analysis

Clampfit (V10.2, Molecular Devices), Excel 2003 and GraphPad Prism 5.0 were used for the data analysis. The calculation formula of the current:

$$I/I_{control}=Bottom+(Top-Bottom)/(1+10^{\wedge}((LogIC50-Log\ C)*Hillslope)$$

TABLE 10

| 11.4. Test results and conclusions: | | | |
|---|---|---|---|
| Compounds | $IC_{50}$ (μM) | HillSlope | Number of cells |
| Amitriptyline | 3.56 | 0.93 | 4 |
| 3a | >10.00 | — | 2 |
| 3b | >30.00 | — | 2 |
| 7b | >10.00 | — | 2 |
| GS-7340 | >10.00 | — | 2 |

Conclusion: the IC50 of compounds 3a and 3b were comparative to those of GS-7340 and 7b in the hERG test, and they were all above 10 μM, which were safe regarding to the cardiotoxicity, and met the general requirement of the hERG data for further research of the compounds during the new drug research and development.

Test example 6: In vivo metabolism and tissue distribution test in mice 12.1. Test animals, drug preparation methods, and dosage regimens 12 ICR mice (male, body weight 30±5 g, purchased from the Vital River animal center) were randomly divided into 4 groups, 3 for each group, fasted for 12 h before drug administration, with freely drinking during the fasting. Precisely weighing 30 mg of compound 3 on the analytical balance, adding 100 μL of 75% ethanol for dissolution, further adding saline to 6 mL, the mixture was vortexed to be uniformly mixed and carried out with ultrasonic processing for further use. The dose of the Tenofovir prodrug was 50 mg/kg, and the administration quantity was 10 mL/kg.

12.2. The sample collection protocols and the treatment methods

The sample collection protocols: after administration by gastric gavage, each 0.5 mL of blood was taken from the orbit at 15 min, 30 min, 1 h, and 3 h; the mice were sacrificed, and the liver tissues were taken, washed cleanly, and weighed; normal saline was added to the liver with a proportion of 1:1, homogenized, and stored in the refrigerator at −40° C. for test.

Treatment method for the plasma samples: 100 μL of the mouse plasma was taken and placed in a 1.5 mL plastic EP tube, 100 μL solution of internal standard (200 ng/ml theophylline) solution was added, 600 μL acetonitrile was added, vortex shaking for 2 min, centrifuged for 3 min (12500 rpm), the supernatant was taken, purged with nitrogen to dryness, and dissolved again with 100 μL of mobile phase (water:methanol=95:5), and the injection volume was 10 μL.

Treatment method for the tissue samples: 200 μL of the mouse tissue samples were taken and placed in a 1.5 mL plastic EP tube, 100 μL solution of internal standard (200 ng/ml theophylline) solution was added, 600 μL acetonitrile was added, vortex shaking for 2 min, centrifuged for 3 min (12500 rpm), the supernatant was taken, purged with nitrogen to dryness, and dissolved again with 100 μL of mobile phase (water:methanol=95:5), and the injection volume was 20μL.

12.3. Method for sample analysis

The Thermo TSQquantum LC-MS and chromatograph column Thermo Hypersil GOLD (2.1×150 mm) were used, the internal standard was Theophylline, gradient elution and analysis were carried out after the HPLC-MS injection, the retention times and peak areas of the internal standard, compound 1 and the metabolic product of Tenofovir (TFV) were recorded, and the SRM quantitative detection method was used for the analysis.

TABLE 11

| 12.4. Analysis results of the sample and conclusions | | | |
|---|---|---|---|
| Compounds (MS) | $C_{plasma}$ (nmol/mL) | $C_{liver\ tissue}$ (nmol/mL) | Liver tissue selectivity ($C_{liver\ tissue}/C_{plasma}$) |
| TFV (287) | 0.075 | 67.251 | 896 |
| Compound 3 (490) | 0.104 | 0.375 | 3.61 |
| Interior label (180) | 1.11 | 1.11 | 1 |

$C_{(compound\ 3+TFV)\ liver\ tissue}/C_{(compound\ 3+TFV)\ plasma} = 377$
$C_{TFV\ plasma}/C_{compound\ 3\ plasma} = 0.72$
$C_{TFV\ liver\ tissue}/C_{compound\ 3\ liver\ tissue} = 166$ The results showed that after 3 h, the concentrations of compound 3 and its metabolic product of Tenofovir TFV in the liver were both higher than those in the blood, and the overall concentration of both in the liver is 377 times of that in the blood, demonstrating that compound 3 could be effectively enriched in the liver. Meanwhile, the concentration of TFV in the blood was only 0.72 times of that of the parent drug compound 3, while the concentration of the parent drug TFV in the liver was 166 times of that of the prodrug compound 3, demonstrating that compound 3 was relatively stable in the mouse blood, and effectively metabolized into the active parent drug Tenofovir in the liver. Therefore, compound 3 had blood stability and liver-targeting anti-HBV activity in the animal test in vivo.

The invention claimed is:

1. A tenofovir monobenzyl ester phosphamide compound of the general formula X, and the hydrate, solvate, pharmaceutically acceptable salt thereof or the resolved single isomer thereof,

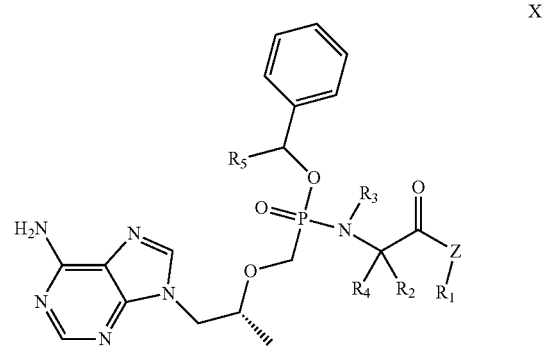

X wherein Z is selected from O, S, Se, NH— or CH$_2$—,
$R_1$, $R_2$, $R_3$, $R_4$, and $R_5$ are each independently selected from H, substituted or unsubstituted $C_1$-$C_{10}$ linear alkyl, $C_3$-$C_{10}$ branched alkyl, $C_3$-$C_{10}$ cycloalkyl, and $C_6$-$C_{10}$ aryl or heteroaryl, wherein the substitution is one to three hetero atoms independently selected from O, S, N and Se, or a substituted or unsubstituted 3-8 membered ring formed by $R_1$ and $R_2$, $R_1$ and $R_3$, or $R_2$ and $R_3$ with the moiety they are attached to, form.

2. The tenofovir monobenzyl ester phosphamide compound according to claim 1, wherein, Z is selected from O or S, $R_1$, $R_2$, $R_3$, $R_4$, and $R_5$ are each independently selected from H, substituted or unsubstituted $C_1$-$C_6$ linear alkyl, $C_3$-$C_6$ branched alkyl, $C_3$-$C_6$ cycloalkyl, and $C_6$-$C_{10}$ aryl or heteroaryl.

3. The tenofovir monobenzyl ester phosphamide compound according to claim 2, wherein, Z is selected from O, $R_1$, $R_2$, $R_3$, $R_4$, and $R_5$ are each independently selected from H, substituted or unsubstituted $C_1$-$C_6$ linear alkyl, $C_3$-$C_6$ branched alkyl, and $C_6$-$C_{10}$ aryl.

4. A compound selected from compounds 1, 2, 3, 4, 5, and 6

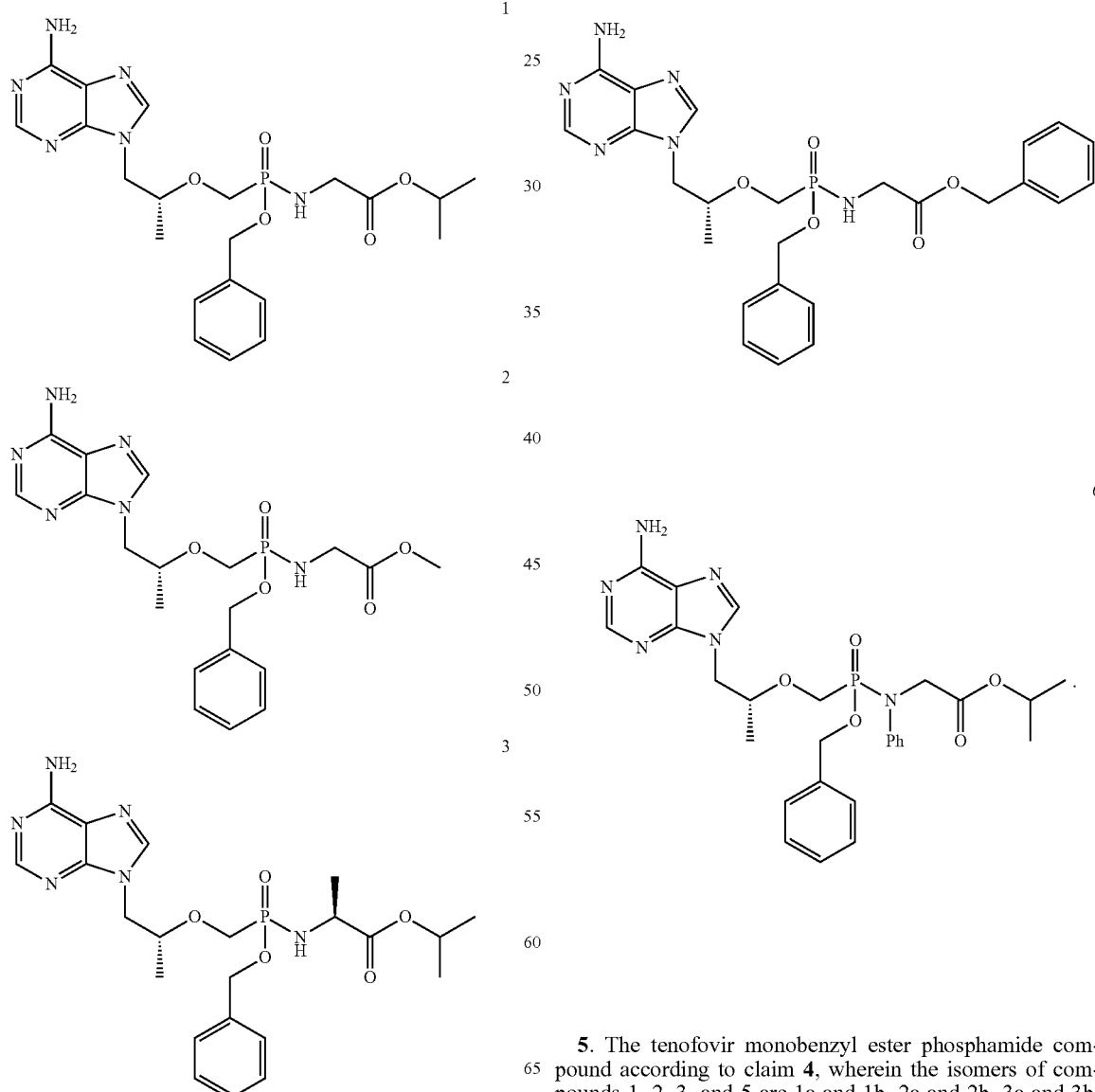

5. The tenofovir monobenzyl ester phosphamide compound according to claim 4, wherein the isomers of compounds 1, 2, 3, and 5 are 1a and 1b, 2a and 2b, 3a and 3b, and 5a and 5b, respectively, with the structures of:

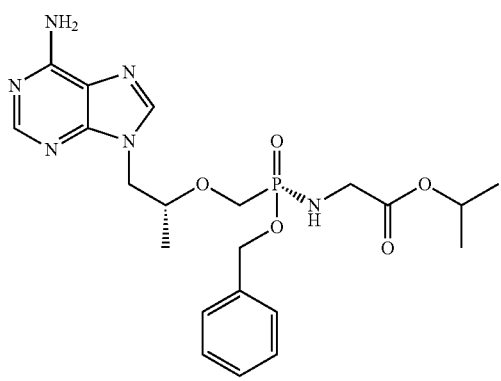
1a
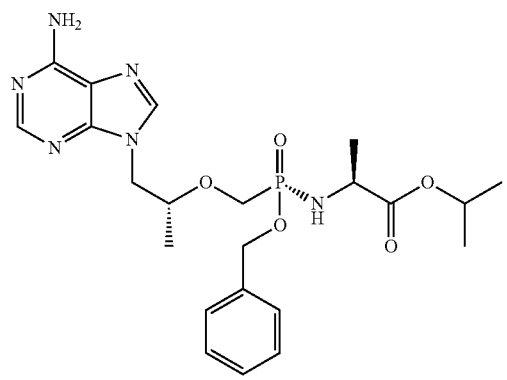
3a
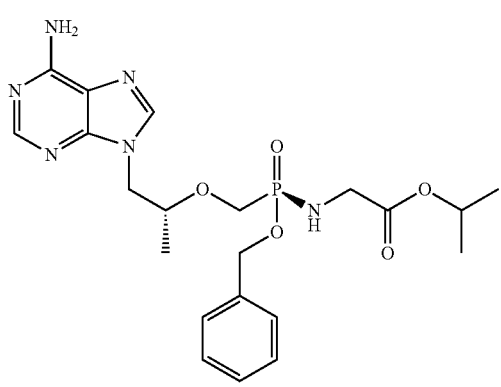
1b
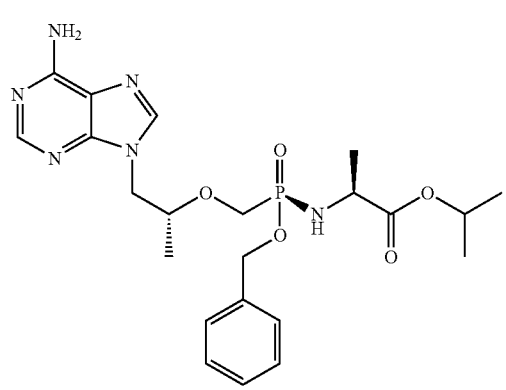
3b
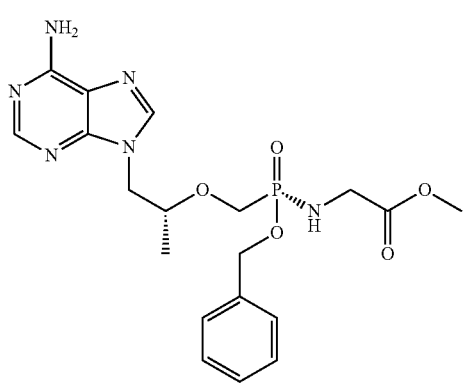
2a
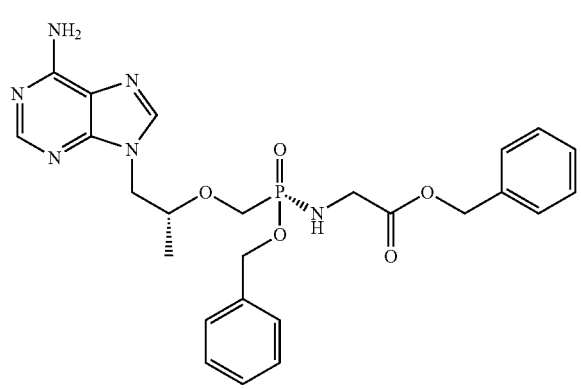
5a
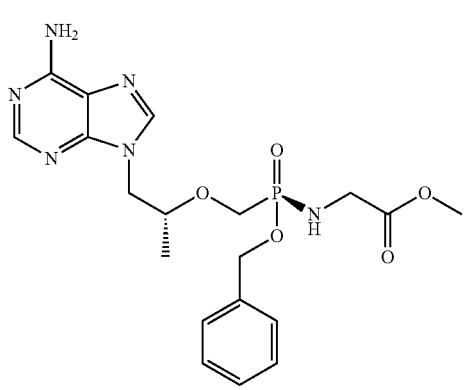
2b
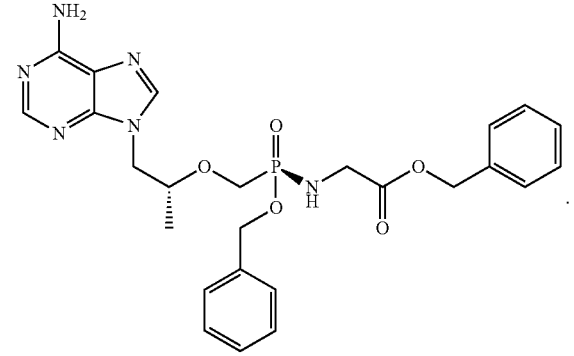
5b
6. A preparation method of the tenofovir monobenzyl ester phosphamide compound according to claim 1, characterized in that the method includes the following steps:

A: Tenofovir is reacted with benzyl halide or benzyl alcohol in the presence of bases to produce the intermediate of the tenofovir monobenzyl ester;

B: the intermediate of the tenofovir monobenzyl ester is reacted with various compounds containing the terminal NH group, preferably ester compounds of amino acid or amide compounds of amino acid, to produce the tenofovir monobenzyl ester phosphamide compound of the present invention.

7. The preparation method of the tenofovir monobenzyl ester phosphamide compound according to claim 6, wherein, Tenofovir of step A is preferably reacted with benzyl bromide or benzyl alcohol, and the bases can be various inorganic or organic bases, preferably organic bases.

8. A pharmaceutical composition, characterized in that the pharmaceutical composition comprises the tenofovir monobenzyl ester phosphamide compound according to claim 1, or the hydrate thereof, or the solvate thereof, or the pharmaceutically acceptable salt thereof or the resolved single isomer thereof; wherein, the pharmaceutical composition also comprises a pharmaceutically acceptable carrier.

9. Use of the tenofovir monobenzyl ester phosphamide compound according to claim 1, or the hydrate thereof, or the solvate thereof, or the pharmaceutically acceptable salt thereof or the resolved single isomer thereof in the preparation of the drugs for treating diseases of viral infections.

10. Use of the tenofovir monobenzyl ester phosphamide compound according to claim 9, or the hydrate thereof, or the solvate thereof, or the pharmaceutically acceptable salt thereof or the resolved single isomer thereof in the preparation of the drugs for treating AIDS infection or hepatitis B or diseases caused by the hepatitis B virus.

11. A preparation method of the tenofovir monobenzyl ester phosphamide compound according to claim 3, characterized in that the method includes the following steps:

A: Tenofovir is reacted with benzyl halide or benzyl alcohol in the presence of bases to produce the intermediate of the tenofovir monobenzyl ester;

B: the intermediate of the tenofovir monobenzyl ester is reacted with various compounds containing the terminal NH group, preferably ester compounds of amino acid or amide compounds of amino acid, to produce the tenofovir monobenzyl ester phosphamide compound of the present invention.

12. A preparation method of the tenofovir monobenzyl ester phosphamide compound according to claim 4, characterized in that the method includes the following steps:

A: Tenofovir is reacted with benzyl halide or benzyl alcohol in the presence of bases to produce the intermediate of the tenofovir monobenzyl ester;

B: the intermediate of the tenofovir monobenzyl ester is reacted with various compounds containing the terminal NH group, preferably ester compounds of amino acid or amide compounds of amino acid, to produce the tenofovir monobenzyl ester phosphamide compound of the present invention.

13. A preparation method of the tenofovir monobenzyl ester phosphamide compound according to claim 5, characterized in that the method includes the following steps:

A: Tenofovir is reacted with benzyl halide or benzyl alcohol in the presence of bases to produce the intermediate of the tenofovir monobenzyl ester;

B: the intermediate of the tenofovir monobenzyl ester is reacted with various compounds containing the terminal NH group, preferably ester compounds of amino acid or amide compounds of amino acid, to produce the tenofovir monobenzyl ester phosphamide compound of the present invention.

14. The preparation method of the tenofovir monobenzyl ester phosphamide compound according to claim 12, wherein, Tenofovir of step A is preferably reacted with benzyl bromide or benzyl alcohol, and the bases can be various inorganic or organic bases, preferably organic bases.

15. The preparation method of the tenofovir monobenzyl ester phosphamide compound according to claim 13, wherein, Tenofovir of step A is preferably reacted with benzyl bromide or benzyl alcohol, and the bases can be various inorganic or organic bases, preferably organic bases.

16. A pharmaceutical composition, characterized in that the pharmaceutical composition comprises the tenofovir monobenzyl ester phosphamide compound according to claim 5, or the hydrate thereof, or the solvate thereof, or the pharmaceutically acceptable salt thereof or the resolved single isomer thereof; wherein, the pharmaceutical composition also comprises a pharmaceutically acceptable carrier.

17. Use of the tenofovir monobenzyl ester phosphamide compound according to claim 4, or the hydrate thereof, or the solvate thereof, or the pharmaceutically acceptable salt thereof or the resolved single isomer thereof in the preparation of the drugs for treating diseases of viral infections.

18. Use of the tenofovir monobenzyl ester phosphamide compound according to claim 5, or the hydrate thereof, or the solvate thereof, or the pharmaceutically acceptable salt thereof or the resolved single isomer thereof in the preparation of the drugs for treating diseases of viral infections.

19. Use of the tenofovir monobenzyl ester phosphamide compound according to claim 17, or the hydrate thereof, or the solvate thereof, or the pharmaceutically acceptable salt thereof or the resolved single isomer thereof in the preparation of the drugs for treating AIDS infection or hepatitis B or diseases caused by the hepatitis B virus.

20. Use of the tenofovir monobenzyl ester phosphamide compound according to claim 18, or the hydrate thereof, or the solvate thereof, or the pharmaceutically acceptable salt thereof or the resolved single isomer thereof in the preparation of the drugs for treating AIDS infection or hepatitis B or diseases caused by the hepatitis B virus.

* * * * *